(12) United States Patent
Iwakiri

(10) Patent No.: US 8,581,221 B2
(45) Date of Patent: Nov. 12, 2013

(54) IMAGE INFORMATION DETECTING APPARATUS

(75) Inventor: Naoto Iwakiri, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 1708 days.

(21) Appl. No.: 11/447,924

(22) Filed: Jun. 7, 2006

(65) Prior Publication Data

US 2006/0280381 A1 Dec. 14, 2006

(30) Foreign Application Priority Data

Jun. 7, 2005 (JP) ................................. 2005-166566

(51) Int. Cl.
*G01N 23/04* (2006.01)
*G03C 5/16* (2006.01)
*G21K 4/00* (2006.01)

(52) U.S. Cl.
USPC ........................... 250/580; 250/582; 250/584

(58) Field of Classification Search
USPC ....................................................... 250/580
See application file for complete search history.

(56) References Cited

U.S. PATENT DOCUMENTS

| | | | | |
|---|---|---|---|---|
| 5,877,501 A * | 3/1999 | Ivan et al. | ................ | 250/370.09 |
| 6,268,614 B1 | 7/2001 | Imai | | |
| 7,015,478 B2 | 3/2006 | Yamamoto | | |
| 7,250,608 B2 * | 7/2007 | Ozeki | ....................... | 250/370.08 |
| 2002/0053650 A1 * | 5/2002 | Iwakiri | ......................... | 250/588 |
| 2004/0079908 A1 * | 4/2004 | Ohkubo | ....................... | 250/582 |
| 2004/0114725 A1 * | 6/2004 | Yamamoto | ..................... | 378/189 |
| 2006/0017028 A1 * | 1/2006 | Ohara et al. | .................. | 250/580 |
| 2006/0169907 A1 * | 8/2006 | Shinden | .................... | 250/370.09 |

FOREIGN PATENT DOCUMENTS

| | | |
|---|---|---|
| JP | 7-140255 A | 6/1995 |
| JP | 2003-210444 A | 7/2003 |
| JP | 2004-173907 A | 6/2004 |
| JP | 2004246288 A | 9/2004 |

OTHER PUBLICATIONS

Japanese Office Action dated Jun. 22, 2010, corresponding to Japanese Patent Application No. 2005-166566.
Office Action issued Oct. 26, 2010 corresponding to Japanese Counterpart Application No. 2005-166566.
Japanese Office Action issued in corresponding Japanese Application No. 2011-013670, dated Sep. 11, 2012, 2 pages in English and Japanese.

* cited by examiner

*Primary Examiner* — Walter L Lindsay, Jr.
*Assistant Examiner* — Jessica L Eley
(74) *Attorney, Agent, or Firm* — Sughrue Mion, PLLC

(57) ABSTRACT

An image information detecting apparatus with an image information detecting unit that receives recording light representing image information, and records the image information by storing electric charges generated in the unit by the recording light. The apparatus further includes a wireless communication means operable for transmission to an external device; a wire communication means operable for transmission to the external device through a detachable communication cable; a wire transmission setting means for setting the wire communication means operable for transmission; and a wireless transmission prohibiting means. The wireless transmission prohibiting means prohibits wireless transmission from the wireless communication means when the wire communication means is set operable for transmission by the wire transmission setting means.

10 Claims, 2 Drawing Sheets

IMAGE INFORMATION DETECTING APPARATUS

BACKGROUND OF THE INVENTION

1. Field of the Invention

The present invention relates generally to an image information detecting apparatus with an image information detecting unit that receives recording light representing image information, and records the image information by storing electric charges generated therein by the recording light. More specifically, the present invention relates to an image information detecting apparatus with a wireless transmission capability.

2. Description of the Related Art

Today, in X-ray imaging for medical diagnosis or the like, various image information detecting devices with an image information detecting unit that receives recording light (X-ray, or the like) representing image information, and records the image information by storing electric charges generated therein by the recording light are proposed and put into practical use as described, for example, in U.S. Pat. No. 6,268,614.

Most of these image information detecting devices include a charge readout means for reading out the electric charges stored therein as electrical signals. From the aspect of charge readout process, the optical-scan readout method in which the electric charges are read out by scanning the detecting unit with light beams, and electrical-scan readout method in which the electric charges are read out by electrically scan-driving TFTs (thin film transistors) or the like incorporated in the detecting unit, are widely known.

Recently, development of cassette type image information detecting device accommodated in a case, which is mountable and usable with an existing X-ray imaging machine or the like, has been underway, and functional improvement is anticipated. Further, image information detecting devices that include a communication cable for outputting electrical signals readout from the image information detecting unit to an external image processing unit are also known.

Further, image information detecting devices that include a wireless transmission means that wirelessly transmits electrical signals read out from the image information detecting unit to an external image processing device, thereby ensuring setting freedom of the device to an X-ray imaging machine without hindered by the communication cable, are also known as described, for example, in Japanese Unexamined Patent Publication Nos. 7(1995)-140255 and 2003-210444.

The image information detecting device with a wireless transmission capability described in Japanese Unexamined Patent Publication Nos. 7 (1995)-140255 and 2003-210444, however, has only the wireless transmission means as a transmission means to an external device. Consequently, it has a problem that it is unable to transmit to the external device when wireless transmission is difficult, inappropriate, or the like.

In view of the circumstances described above, it is an object of the present invention to provide an image information detecting apparatus with a wireless transmission capability, and further operable for transmission to an external device when wireless transmission is difficult, inappropriate, or the like.

SUMMARY OF THE INVENTION

An image information detecting apparatus according to the present invention comprises:

an image information detecting unit that receives recording light representing image information, and records the image information by storing electric charges generated therein by the recording light;

a wireless communication means operable for transmission to an external device;

a wire communication means operable for transmission to the external device through a detachable communication cable;

a wire transmission setting means for setting the wire communication means operable for transmission;

a wireless transmission prohibiting means for prohibiting wireless transmission from the wireless communication means when the wire communication means is set operable for transmission by the wire transmission setting means. The referent of "detachable communication cable" as used herein means a communication cable which is connectable to and detachable from the wire communication means.

As for the transmission contents to be transmitted to the external device, various information items may be conceivable. More specifically, an image information recording ready signal, an image information recording completion signal, and, if an image information readout means is provided, the image information signals read out thereby may be included in the contents. Further, the transmission contents may include imaging information associated with the image information, and the like.

The wireless transmission prohibiting means may be a means that prohibits the wireless transmission from the wireless communication means by terminating power supply thereto when the wire communication means is set operable for transmission by the wire transmission setting means.

If a configuration is adopted in which a communication cable detection means for detecting connection of the communication cable to the wire communication means is further provided, the wire transmission setting means may be a means that sets the wire communication means operable for transmission when the connection of the communication cable is detected by the communication cable detection means.

Further, if a configuration is adopted in which a receiving means operable for reception from external equipment is further provided, the wire transmission setting means may be a means that sets the wire communication means operable for transmission based on control through communication from the external equipment. Here, the "external equipment" may be a device identical with the "external device" described above.

Still further, if a configuration is adopted in which a manual entry means such as a switch or a touch panel is provided on the body of the image information detecting apparatus, the wire communication setting means may be a means that sets the wire communication means operable for transmission by manual control through the manual entry means.

The image information detecting apparatus of the present invention includes: a wireless communication means operable for transmission to an external device; a wire communication means operable for transmission to the external device through a detachable communication cable; and a wire transmission setting means for setting the wire communication means operable for transmission. This allows transmission to the external device through the wire communication means by setting the wire communication means operable for transmission by the wire transmission setting means and prohibiting wireless transmission from the wireless communication means when wireless transmission is difficult, inappropriate, or the like. This improves the convenience of the apparatus, and may prevent, in particular, accidental wireless transmission when the wireless transmission is inappropriate.

If the wireless transmission prohibiting means is a means that prohibits the wireless transmission from the wireless communication means by terminating power supply thereto when the wire communication means is set operable for transmission by the wire transmission setting means, the power consumption of the apparatus may be reduced when wireless transmission is disabled.

If a configuration is adopted in which a communication cable detection means for detecting connection of the communication cable to the wire communication means is further provided, and the wire transmission setting means sets the wire communication means operable for transmission when the connection of the communication cable is detected by the communication cable detection means, the wire communication means may be set operable for transmission by simply connecting the communication cable to the wire communication means, so that the operational procedure for wire transmission is simplified.

If a configuration is adopted in which a receiving means operable for reception from external equipment is further provided, and the wire transmission setting means sets the wire communication means operable for transmission based on control through communication from the external equipment, the structure of the apparatus may be simplified without requiring any function for switching the communication means, such as a switch or the like, on the body of the apparatus.

DESCRIPTION OF THE PREFERRED EMBODIMENTS

Figure 1:
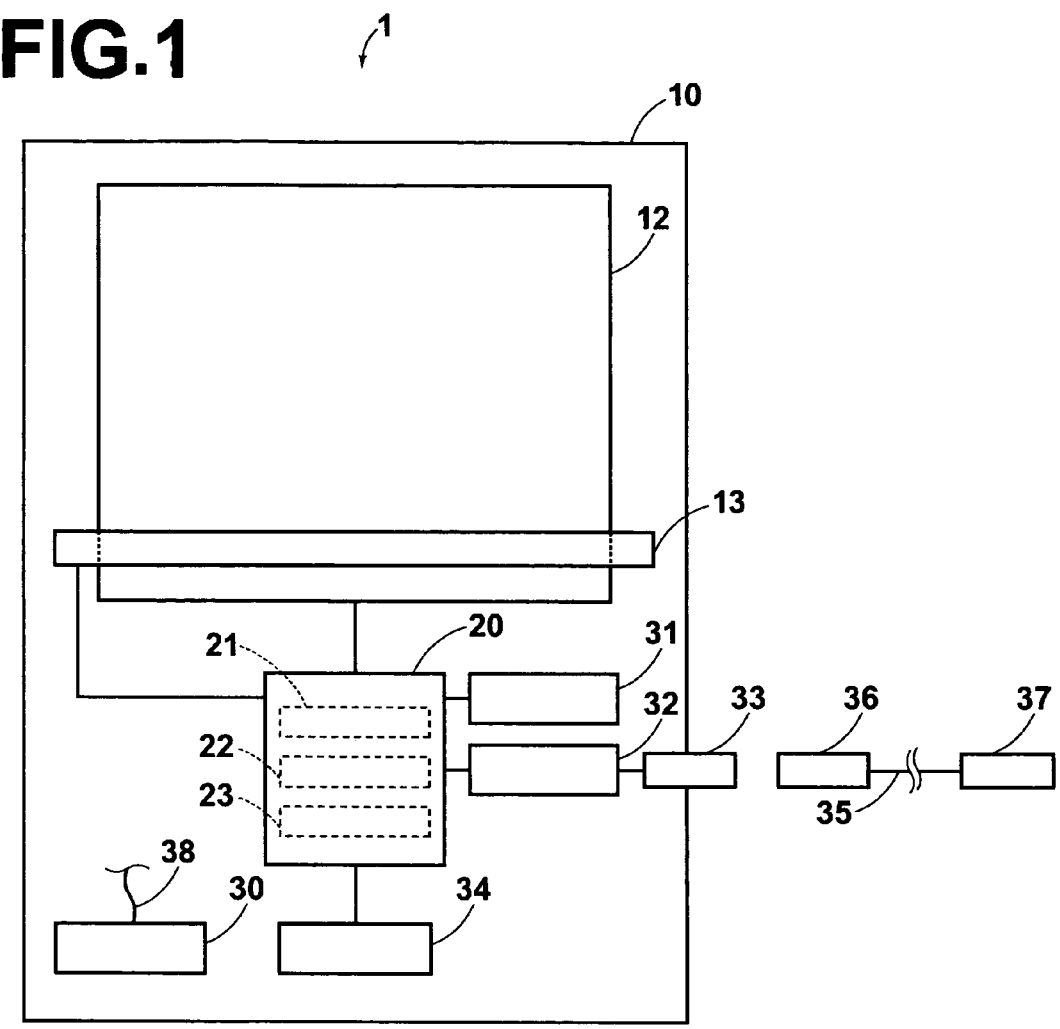
FIG. 1 is a block diagram of the image information detecting apparatus according to a first embodiment of the present invention, illustrating the structure and circuit blocks of the relevant part thereof.

Hereinafter, embodiments of the present invention will be described in detail with reference to the accompanying drawings. FIG. 1 is a block diagram of a cassette type image information detecting apparatus according to a first embodiment of the present invention, illustrating the structure and circuit blocks of the relevant part thereof. The image information detecting apparatus 1 is used for medical X-ray imaging. It has a substantially rectangular solid shaped case 10 which includes therein: an image information detecting unit 12; a readout light emitting unit 13; a control unit 20; a battery 30 for supplying power to respective units or sections; a wireless communication unit 31; a wire communication unit 32; a connection terminal 33 that connects the wire communication unit 32; and a communication selection switch 34 for selecting wireless or wire transmission. The connection terminal 33 is connectable to a connection terminal 36 of a communication cable 35 which is connected to an external system controller 37. The system controller 37 is a controller capable of providing wireless and wire communication, acting as the external device or external equipment of the present invention. It may be provided on the X-ray imaging machine, or in a control room which is different from the X-ray imaging machine room, or the like.

The image information detecting unit 12 receives X-ray exposure, which is the recording light transmitted through a subject, and records image information of the subject represented by the X-ray by storing electric charges generated therein by the X-ray as the latent image charges. The unit 12 includes the following layers in the order listed below: a first electrode layer that transmits the X-ray; a recording photoconductive layer that shows electrical conductivity when exposed to the X-ray; a charge transport layer that acts substantially as an insulator against the latent image charges and substantially a conductor for transport charges of the polarity opposite to that of the latent image charges; a readout photoconductive layer that shows electrical conductivity when exposed to readout light; and a second electrode layer that transmits the readout light.

When recording image information, X-ray is irradiated on the image information detecting unit from the side of the first electrode layer with a high voltage being applied between the first and second electrode layers to provide an electric field therebetween, and an amount of electric charges corresponding to the dose of X-ray irradiated on the image information detecting unit is stored in a storage section formed at the interface between the recording photoconductive layer and charge transport layer as the latent image charges. The image information recorded in the image information detecting unit 12 is read out by scanning the image information detecting unit 12 with readout light emitted from the readout light emitting unit 13.

The control unit 20 includes a recording/readout control section 21 for causing an electric field to be applied to the image information detecting unit 12 when recording image information, image signals to be read out according to the image information recorded in the image information detecting unit 12 through optical scanning of the image information detecting unit 12 with the readout light emitting unit 13, and image processing to be performed on the readout image signals; a memory 22 for storing the processed image signals; and a communication control section 23 for setting the wire communication unit 32 operable for transmission when wire communication is selected by the communication selection switch 34, and setting the wireless communication unit 31 operable for transmission when wireless communication is selected thereby. The communication control section 23 prohibits wireless transmission from the wireless communication unit 31 when the wire communication unit 32 is set operable for transmission, acting both as the wire transmission setting means and wireless transmission prohibiting means of the present invention.

Prior to initiating X-ray imaging, the radiographer selects through the communication selection switch 34 either the wire communication unit 32 or wireless communication unit 31 for transmission. Normally, the wireless communication unit 31 is selected for transmission, since the communication cable 35 is not connected to the image information detecting apparatus 1 in order to ensure setting freedom thereof. The communication control section 23 sets the wireless communication unit 31 operable for reception and transmission when wireless transmission is selected by the communication selection switch 34.

On the other hand, if wireless transmission is difficult, inappropriate, or the like, transmission using the wire communication unit 32 is selected. In this case, the connection terminal 36 of the communication cable 35 is connected to the connection terminal 33 in advance. The communication control section 23 sets the wire communication unit 32 operable for reception and transmission when wire transmission is selected by the communication selection switch 34, and disables the wireless transmission function of the wireless communication unit 31. Here, the wireless transmission function of the wireless communication unit 31 is disabled, but the receiving function thereof is maintained for normal operation.

The operation of the image information detecting apparatus 1 will be described in detail with reference to an example case where wire communication is selected. Various data, including imaging menu, ID information, application voltage required for image recording, readout speed, and the like, are inputted to the control unit 20 from the system controller 37 through the communication cable 35, connection terminal 36, and connection terminal 33. Further, during the time period from the time when the X-ray is ready to be irradiated to the time just after the X-ray is irradiated, an X-ray ready signal is inputted to the control unit 20 from the system controller 37, and when the X-ray is irradiated, an X-ray irradiation signal is also inputted to the control unit 20 from the system controller 37. The control unit 20 also performs overall operation control of the image information detecting apparatus 1. Here, power is supplied to each unit or section from the battery 30 through a power supply wiring 38. In FIG. 1, however, the detailed wiring state of the power supply wiring 38 is omitted for clarity.

Hereinafter, the operation of the image information detecting cassette 1 according to the present embodiment will be described. First, recording of image information and reading out of the image information will be described. Prior to initiating X-ray imaging, various data, including imaging menu, ID information, application voltage required for image recording, readout speed, and the like, are inputted to the control unit 20 from the system controller 37 through the communication cable 35, connection terminal 36, and connection terminal 33. The control unit 20 stores these data in the memory 22, and uses them as required by reading out from the memory 22.

During the time period from the time when the X-ray is ready to be irradiated to the time just after the X-ray is irradiated, an X-ray ready signal is inputted to the control unit 20 from the system controller 37 through the communication cable 35 and wire communication unit 32. Further, when the X-ray is irradiated, an X-ray irradiation signal is inputted to the control unit 20.

When the X-ray ready signal is inputted to the control unit 20, the control unit 20 controls the recording/readout control section 21 to cause a recording high voltage to be applied to the image information detecting unit 12. Then, X-ray transmitted through the subject is irradiated on the image information detecting unit 12, and an amount of electric charges corresponding to the dose of X-ray irradiated thereon is stored therein as the latent image charges. In reading out operation, the control unit 20 controls the recording/readout control section 21 to cause the image information detecting section 12 to be scanned with the readout light emitted from the readout light emitting unit 13 so that the image information recorded in the image information detecting section 12 is read out, which is processed and tentatively stored in the memory 22. Thereafter, the image information stored in the memory 22 is sent to the system controller 37 by the control unit 20 through the wire communication unit 32, connection terminal 33, connection terminal 36, and communication cable 35.

As is clear from the above description, the image information detecting apparatus 1 includes the wireless communication unit 31 operable for transmission to the system controller which is an external device, and wire communication unit 32 operable for transmission to the system controller through the detachable communication cable 35. This allows transmission to the system controller through the wire communication unit 32 by setting the wire communication unit 32 operable for transmission and prohibiting wireless transmission from the wireless communication unit 31 when wireless transmission is difficult, inappropriate, or the like. This improves the convenience of the apparatus, and, in particular, accidental wireless transmission may be prevented when the wireless transmission is inappropriate.

In the present embodiment, switching between wireless and wire transmission is implemented by the communication selection switch 34 provided on the body of the image information detecting apparatus 1. But, the present embodiment is not limited to this, and a configuration may be adopted in which the switching between the wireless and wire communication is implemented by the signal received by the wire communication unit 32 or wireless communication unit 31. In this case, the structure of the image information detecting apparatus 1 may be simplified without requiring the communication selection switch 34. Further, if the communication method is to be switched through the wire communication unit 32, switching of the communication unit may be implemented even if the transmission and receiving functions of the wireless communication unit 31 are disabled when the wire communication unit 32 is used.

Figure 2:
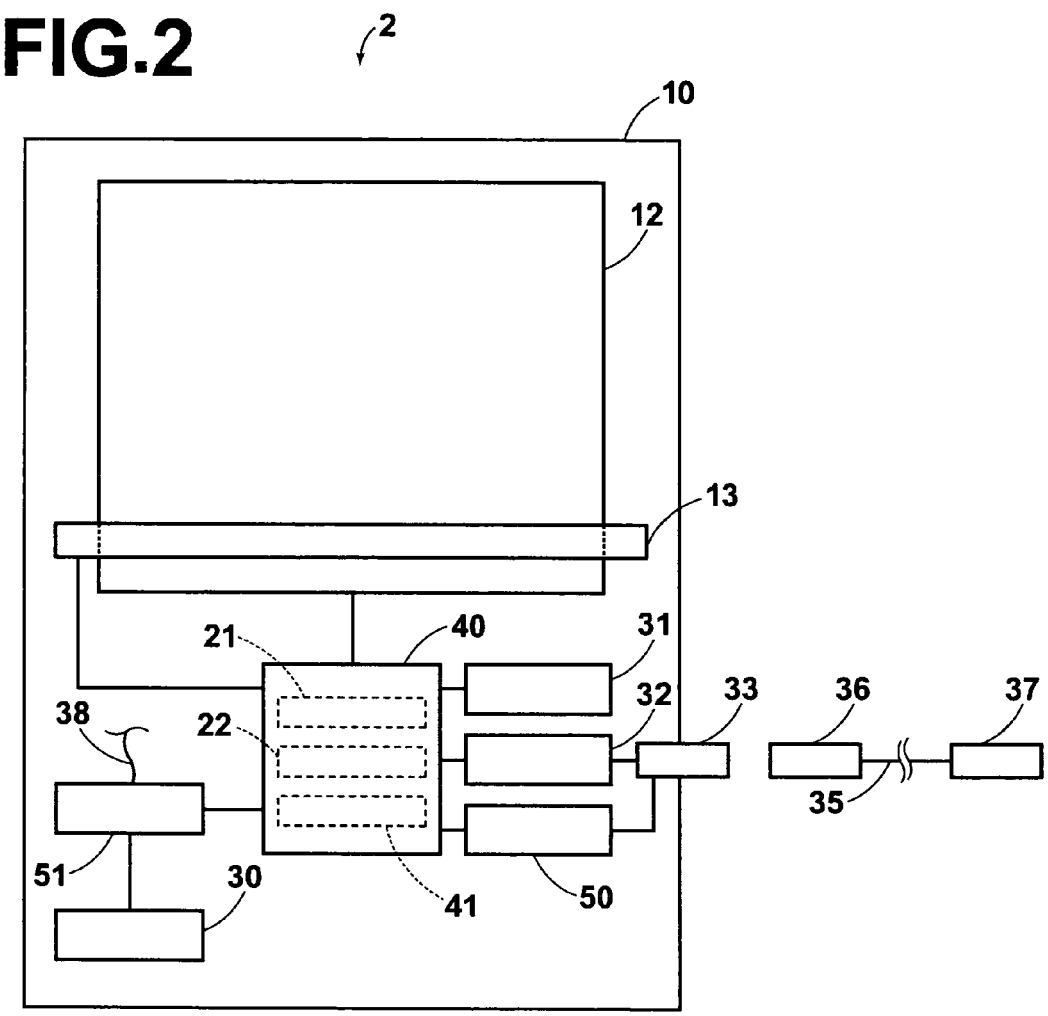
FIG. 2 is a block diagram of the image information detecting apparatus according to a second embodiment of the present invention, illustrating the structure and circuit blocks of the relevant part thereof.

Hereinafter, an image information detecting apparatus 2 according to a second embodiment of the present invention will be described with reference to FIG. 2. In FIG. 2, components identical to those shown in FIG. 1 are given the same reference numerals, and will not be elaborated upon further here unless otherwise specifically required.

FIG. 2 is a block diagram of the image information detecting apparatus 2, illustrating the structure and circuit blocks of the relevant part thereof. The image information detecting apparatus 2 is a cassette type apparatus used for medical X-ray imaging. It has the case 10 which includes therein: the image information detecting unit 12; the readout light emitting unit 13; a control unit 40; the battery 30 for supplying power to respective units or sections; a power supply control unit 51 for controlling power supply from the battery 30; the wireless communication unit 31; the wire communication unit 32; the connection terminal 33 that connects the wire communication unit 32; and a communication cable detection unit 50 for detecting if the connection terminal 36 of the communication cable 35, which is connected to the system controller 37, is connected to the connection terminal 33.

The control unit 40 includes the recording/readout control section 21 for controlling the recording and reading out of image information; the memory 22; and a communication control section 41 for setting the wire communication unit 32 operable for transmission when connection of the connection terminal 36 of the communication cable 35, which is connected to the system controller 37, to the connection terminal 33 is detected by the communication cable detection unit 50, and setting the wireless communication unit 31 operable for transmission when the connection terminal 36 is detected not to be connected to the connection terminal 33. The communication control section 41 controls the power supply control unit 51 to terminate power supply to the wireless communication unit 31 when the wire communication unit 32 is set operable for transmission, acting both as the wire transmission setting means and wireless transmission prohibiting means of the present invention. When wireless communication is used, power is supplied to each unit or section, and when the wire communication is used, power is supplied to each unit or section other than the wireless communication unit 31 from the battery 30 through the power supply control unit 51 and power supply wiring 38.

Prior to initiating X-ray imaging, the radiographer selects either the wire communication unit 32 or wireless communication unit 31 for transmission by determining whether to connect the connection terminal 36 of the communication cable 35 to the connection terminal 33 of the wire communication unit 32. Normally, the communication cable 35 is not connected to the wire communication unit 32 in order to ensure setting freedom of the image information detecting apparatus 1. Here, the connection terminal 36 of the communication cable 35 is detected not to be connected to the connection terminal 33 by the communication cable detection unit 50, and the wireless communication unit 31 is selected automatically for reception and transmission by the communication control section 41.

On the other hand, if wireless transmission is difficult, inappropriate, or the like, the connection terminal 36 of the communication cable 35 is connected to the connection terminal 33 of the wire communication unit 32 by the radiographer. Here, the connection terminal 36 of the communication cable 35 is detected to be connected to the connection terminal 33 of the wire communication unit 32 by the communication cable detection unit 50, and transmission by the wire communication unit 32 is selected automatically for transmission by the communication control section 41, which at the same time controls the power supply control unit 51 to terminate power supply to the wireless communication unit 31.

The operation of the image information detecting apparatus 2 is identical to that of the image information detecting apparatus 1, so that detailed description thereof will not be repeated here.

As is clear from the above description, the image information detecting apparatus 2 includes the wireless communication unit 31 operable for transmission to the system controller 37, and wire communication unit 32 operable for transmission to the system controller 37 through the detachable communication cable 35. When the communication cable 35 is connected to the wire communication unit 32, the wire communication unit 32 is selected automatically, and power supply to the wireless communication unit 31 is terminated to prohibit wireless transmission. This allows transmission to the system controller 37 through the wire communication unit 32 by setting the wire communication unit 32 operable for transmission and prohibiting wireless transmission from the wireless communication unit 31 when wireless transmission is difficult, inappropriate, or the like. This improves the convenience of the apparatus, and, in particular, accidental wireless transmission may be prevented when the wireless transmission is inappropriate.

Further, when the wire communication unit 32 is set operable for transmission, the power supply to the wireless communication unit 31 is terminated so that the power consumption of the apparatus 2 may be reduced when wireless communication is disabled.

Further, the wire communication unit 32 is selected for transmission when the connection of the communication cable 35 is detected by the communication cable detection unit 50. Thus, the wire communication unit may be automatically set operable for transmission by simply connecting the communication cable 35 to the wire communication unit 32, so that the operational procedure for wire transmission is simplified.

In the embodiments described above, a direct conversion/optical readout type image information detecting unit is used as the image information detecting unit 12. The present invention is not limited to this, and an indirect conversion type image information detecting unit, in which luminescence emitted from a phosphor by receiving recording light is irradiated on a recording photoconductive layer, and signal charges obtained by photoelectrically converting the irradiated luminescence are stored therein, may also be used. Still further, a TFT readout type image information detecting unit, in which electric charges generated in a photoconductive layer that shows electrical conductivity when exposed to recording light are read out by scan driving TFTs, or the like may also be used.

What is claimed is:

1. An image information detecting apparatus, comprising:
    an image information detecting unit which receives recording light representing image information, and which records the image information by storing electric charges generated therein by the recording light;
    a wireless communication means which wirelessly transmits information to and which wirelessly receives information from an external device;
    a wire communication means which communicates with the external device through a communication cable that is detachable from the image information detecting apparatus;
    a wire transmission setting means which enables the wire communication means; and
    a wireless transmission prohibiting means which disables the wireless communication means if the wire communication means is enabled by the wire transmission setting means.

2. The image information detecting apparatus according to claim 1, wherein the wireless transmission prohibiting means prohibits wireless transmission from the wireless communication means by terminating power supply thereto if the wire communication means is enabled by the wire transmission setting means.

3. The image information detecting apparatus according to claim 2, wherein:
    the image information detecting apparatus further includes a communication cable detection means which detects connection of the communication cable to the wire communication means; and
    the wire transmission setting means enables the wire communication means if the connection of the communication cable is detected by the communication cable detection means.

4. The image information detecting apparatus according to claim 3, wherein:
    the image information detecting apparatus further includes a receiving means which receives information from the external device; and
    the wire transmission setting means enables the wire communication means based on a control signal received from the external device.

5. The image information detecting apparatus according to claim 2, wherein:
    the image information detecting apparatus further includes a receiving means which receives information from the external device; and
    the wire transmission setting means enables the wire communication means based on a control signal received from the external device.

6. The image information detecting apparatus according to claim 1, wherein;

the image information detecting apparatus further includes a communication cable detection means which detects connection of the communication cable to the wire communication means; and the wire transmission setting means enables the wire communication means if the connection of the communication cable is detected by the communication cable detection means.

7. The image information detecting apparatus according to claim 6, wherein:

the image information detecting apparatus further includes a receiving means which receives information from the external device; and the wire transmission setting means enables the wire communication means based on a control signal received from the external device.

8. The image information detecting apparatus according to claim 1, wherein:

the image information detecting apparatus further includes a receiving means which receives information from the external device; and the wire transmission setting means enables the wire communication means based on a control signal received, from the external device.

9. The image information detecting apparatus according to claim 1, wherein the wireless communication means is mechanically fixed to the image information detecting apparatus.

10. The image information detecting apparatus according to claim 1, wherein if the wire communication means is enabled by the wire transmission setting means, the wireless transmission prohibiting means automatically disables the wireless communication device.

* * * * *